(12) United States Patent
Le

(10) Patent No.: US 10,221,107 B1
(45) Date of Patent: Mar. 5, 2019

(54) MICROBIAL HUMIC SOIL ENHANCEMENTS

(71) Applicant: Khanh Le, San Jose, CA (US)

(72) Inventor: Khanh Le, San Jose, CA (US)

(73) Assignee: Cisbay Global Inc., San Jose, CA (US)

(*) Notice: Subject to any disclaimer, the term of this patent is extended or adjusted under 35 U.S.C. 154(b) by 0 days.

(21) Appl. No.: 15/786,573

(22) Filed: Oct. 17, 2017

(51) Int. Cl.
| | |
|---|---|
| *A01N 63/00* | (2006.01) |
| *C05G 3/02* | (2006.01) |
| *C05F 11/02* | (2006.01) |
| *C05C 9/00* | (2006.01) |
| *C12M 1/02* | (2006.01) |
| *C12M 1/00* | (2006.01) |
| *C05G 3/00* | (2006.01) |
| *A01C 23/02* | (2006.01) |
| *A01C 23/00* | (2006.01) |

(52) U.S. Cl.
CPC .............. *C05G 3/02* (2013.01); *A01N 63/00* (2013.01); *C05C 9/00* (2013.01); *C05F 11/02* (2013.01); *C05G 3/0076* (2013.01); *C12M 27/00* (2013.01); *C12M 29/00* (2013.01); *C12M 43/00* (2013.01); *A01C 23/008* (2013.01); *A01C 23/023* (2013.01)

(58) Field of Classification Search
None
See application file for complete search history.

(56) References Cited

U.S. PATENT DOCUMENTS

| | | |
|---|---|---|
| 3,719,327 A | 3/1973 | McMahan |
| 6,471,741 B1 | 10/2002 | Reinbergen |
| 2003/0167811 A1* | 9/2003 | Porubcan .................. C05B 1/00 71/6 |
| 2005/0287283 A1 | 12/2005 | Dicks |
| 2008/0213865 A1 | 9/2008 | Lai |
| 2011/0281725 A1 | 11/2011 | Pullen |
| 2014/0234524 A1 | 8/2014 | Parks |

FOREIGN PATENT DOCUMENTS

WO    WO-8702659 A1 *  5/1987  .............. C05F 11/08

\* cited by examiner

*Primary Examiner* — Alton N Pryor
(74) *Attorney, Agent, or Firm* — Tran & Associates

(57) ABSTRACT

A method enhances soil by preparing a microbial solution with microbes, a growth medium, and water; iteratively and selectively breeding generations of microbes to arrive at a predetermined microbial solution in a concentrated form of at least $1\times10^7$ cfu/ml (colony-forming units per milliliter); adding humic acid with amino acids and protein to support an active microbial population to support active and healthy plant growth; and storing the microbial solution as a solid for enriching the soil with micronutrients, microbial cultures and organic materials.

10 Claims, 6 Drawing Sheets

FIG. 1

Figure 2A:
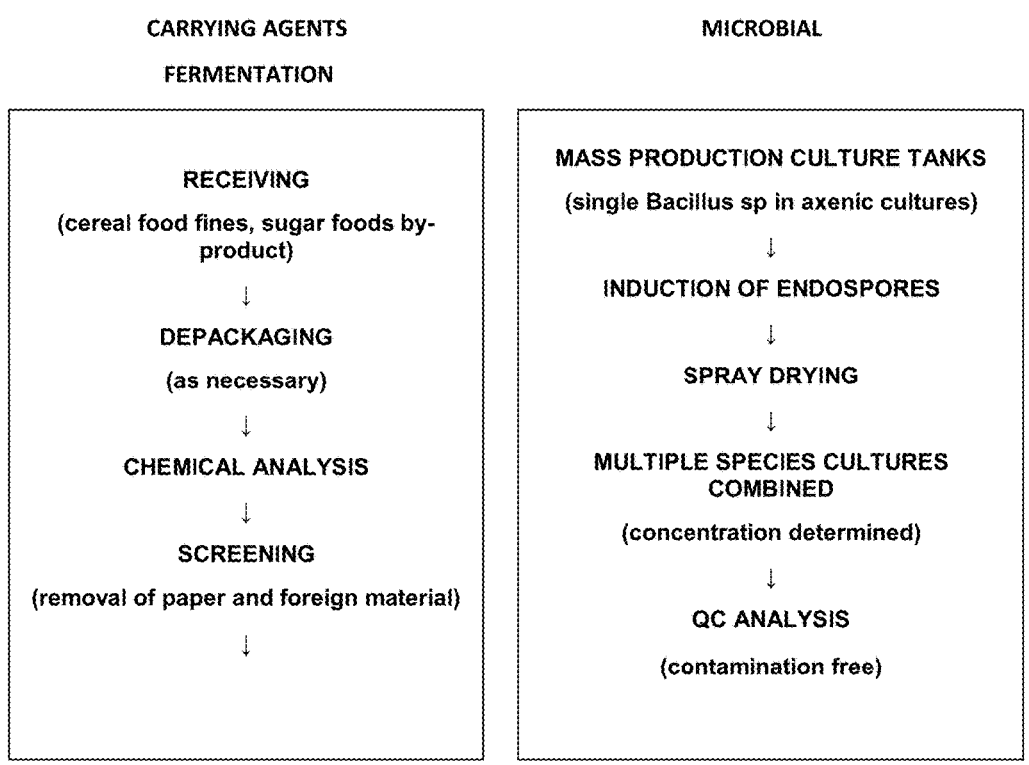
Figure 2B:
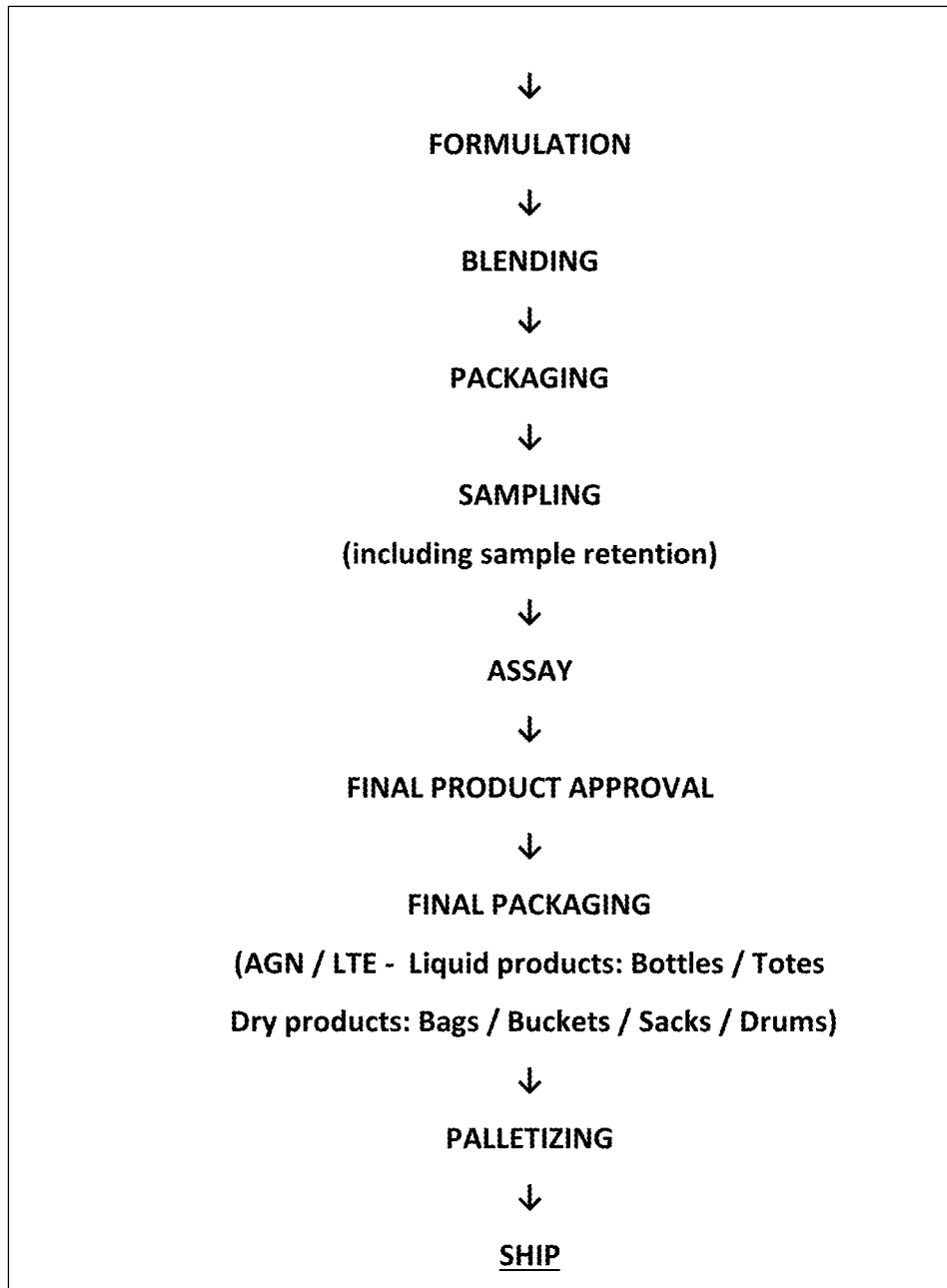

| |
|---|
| 1. Nutrients - Fermentation Media |
| a. Carbon #1 source Dextrose or Glucose |
| b. Carbon #2 source Sucrose |
| 2. Nitrogen – soy protein – Non-GMO |
| 3. Micronutrients – Calcium, Magnesium and Zinc |
| 4. Media is prepared using water supply and sterilized using stream sterilizer at 120 degrees Celsius for 45 minutes based on tank volume. |
| 5. Produce microbial products. At each stage QC methods are applied using standard plate count method for Shigella, E. Coli, Salmonella Yersinia and Psuedomonas beroginosa for their absence. All products are manufactured according to USEPA (United States Environmental Protection Agency) standards. |

| Bacterial Name | Enzyme Production (mm) at 48 hrs. | | | |
|---|---|---|---|---|
| | Protease | Amylase | Cellulase | Lipase |
| B licheniformis | 6 | 0 | 6 | Pos |
| B. pumilus | 6 | 0 | 0 | Pos |
| B. subtilis | 4 | 4 | 0 | Pos |
| B. amyloliquefaciens | 6 | 4 | 4 | Pos |
| B. megaterium | 7 | 5 | 5 | Pos |

MICROBIAL HUMIC SOIL ENHANCEMENTS

BACKGROUND

The present invention relates to microbial enhancements for soil enhancement.

Humic acids are a principal component of humic substances, which are the major organic constituents of soil (humus), peat and coal. It is also a major organic constituent of many upland streams, dystrophic lakes, and ocean water. It is produced by biodegradation of dead organic matter. It is not a single acid; rather, it is a complex mixture of many different acids containing carboxyl and phenolate groups so that the mixture behaves functionally as a dibasic acid or, occasionally, as a tribasic acid. Humic acids can form complexes with ions that are commonly found in the environment creating humic colloids. Humic acids are insoluble in water at acid pH, whereas fulvic acids are also derived from humic substances but are soluble in water across the full range of pH. Humic and fulvic acids are commonly used as a soil supplement in agriculture, and less commonly as a human nutritional supplement. As a nutrition supplement, fulvic acid can be found in a liquid form as a component of mineral colloids. Fulvic acids are poly-electrolytes and are unique colloids that diffuse easily through membranes whereas all other colloids do not.

In a parallel trend, bacterial agricultural microbials are helpful to the crops in a way that they detoxify the soil and fight the root diseases and provide stability to the soil system. They help in nitrogen fixation, phosphate solubilization, iron sequestration, and phytohormone level modulation in crops. Due to these factors, the bacterial segment dominates the agricultural microbials market.

SUMMARY OF THE INVENTION

In one aspect, a method enhances soil by preparing a microbial solution with microbes, a growth medium; iteratively and selectively breeding generations of microbes to arrive at a predetermined microbial solution in a concentrated form of at least $1 \times 10^7$ cfu/ml (colony-forming units per milliliter); and storing the microbial solution in a container for enriching the soil with micronutrients, microbial cultures and organic materials.

In another aspect, an apparatus for enhancing soil includes a tank for a microbial solution with microbes, a growth medium; a sequencer to iteratively and selectively breeding generations of microbes to arrive at a predetermined microbial solution in a highly concentrated form of at least $1 \times 10^7$ cfu/ml (colony-forming units per milliliter); and a pump to dispense the microbial solution into a container to enrich the soil with micronutrients, microbial cultures and organic materials.

Implementations of the above aspects may include one or more of the following. The microbes can be selected from Bacillus (B.) acidiceler, B. acidicola, B. acidiproducens, B. acidocaldarius, B. acidoterrestrisr, B. aeolius, B. aerius, B. aerophilus, B. agaradhaerens, B. agri, B. aidingensis, B. akibai, B. alcalophilus, B. algicola, B. alginolyticus, B. alkalidiazotrophicus, B. alkalinitrilicus, B. alkalisediminis, B. alkalitelluris, B. altitudinis, B. alveayuensis, B. alvei, B. amyloliquefaciens, B. a. subsp. Amyl, aoliquefaciens, B. a. subsp. plantarum, B. amylolyticus, B. andreesenii, B. aneurinilyticus, B. anthracia, B. aquimaris, B. arenosi, B. arseniciselenatis, B. arsenicus, B. aurantiacus, B. arvi, B. aryabhattai, B. asahii, B. atrophaeus, B. axarquiensis, B. azotofixans, B. azotoformans, B. badius, B. barbaricus, B. bataviensis, B. beijingensis, B. benzoevorans, B. beringensis, B. berkeleyi, B. beveridgei, B. bogoriensis, B. boroniphilus, B. borstelensis, B. brevis Migula, B. butanolivorans, B. canaveralius, B. carboniphilus, B. cecembensis, B. cellulosilyticus, B. centrosporus, B. cereus, B. chagannorensis, B. chitinolyticus, B. chondroitinus, B. choshinensis, B. chungangensis, B. cibi, B. circulans, B. clarkii, B. clausii, B. coagulans, B. coahuilensis, B. cohnii, B. composti, B. curdlanolyticus, B. cycloheptanicus, B. cytotoxicus, B. daliensis, B. decisifrondis, B. decolorationis, B. deserti, B. dipsosauri, B. drentensis, B. edaphicus, B. ehimensis, B. eiseniae, B. enclensis, B. endophyticus, B. endoradicis, B. farraginis, B. fastidiosus, B. fengqiuensis, B. firmus, B. flexus, B. foraminis, B. fordii, B. formosus, B. fortis, B. fumarioli, B. funiculus, B. fusiformis, B. galactophilus, B. galactosidilyticus, B. galliciensis, B. gelatini, B. gibsonii, B. ginsengi, B. ginsengihumi, B. ginsengisoli, B. globisporus, B. g. subsp. globisporus, B. g. subsp. marinus, B. glucanolyticus, B. gordonae, B. gottheilii, B. graminis, B. halmapalus, B. haloalkaliphilus, B. halochares, B. halodenitrificans, B. halodurans, B. halophilus, B. halosaccharovorans, B. hemicellulosilyticus, B. hemicentroti, B. herbersteinensis, B. horikoshii, B. horneckiae, B. horti, B. huizhouensis, B. humi, B. hwajinpoensis, B. idriensis, B. indicus, B. infantis, B. infernus, B. insolitus, B. invictae, B. iranensis, B. isabeliae, B. isronensis, B. jeotgali, B. kaustophilus, B. kobensis, B. kochii, B. kokeshiiformis, B. koreensis, B. korlensis, B. kribbensis, B. krulwichiae, B. laevolacticus, B. larvae, B. laterosporus, B. lautus, B. lehensis, B. lentimorbus, B. lentus, B. licheniformis, B. ligniniphilus, B. litoralis, B. locisalis, B. luciferensis, B. luteolus, B. luteus, B. macauensis, B. macerans, B. macquariensis, B. macyae, B. malacitensis, B. mannanilyticus, B. marisflavi, B. marismortui, B. marmarensis, B. massiliensis, B. megaterium, B. mesonae, B. methanolicus, B. methylotrophicus, B. migulanus, B. mojavensis, B. mucilaginosus, B. muralis, B. murimartini, B. mycoides, B. naganoensis, B. nanhaiensis, B. nanhaiisediminis, B. nealsonii, B. neidei, B. neizhouensis, B. niabensis, B. niacini, B. novalis, B. oceanisediminis, B. odysseyi, B. okhensis, B. okuhidensis, B. oleronius, B. oryzaecorticis, B. oshimensis, B. pabuli, B. pakistanensis, B. pallidus, B. pallidus, B. panacisoli, B. panaciterrae, B. pantothenticus, B. parabrevis, B. paraflexus, B. pasteurii, B. patagoniensis, B. peoriae, B. persepolensis, B. persicus, B. pervagus, B. plakortidis, B. pocheonensis, B. polygoni, B. polymyxa, B. popilliae, B. pseudalcalophilus, B. pseudofirmus, B. pseudomycoides, B. psychrodurans, B. psychrophilus, B. psychrosaccharolyticus, B. psychrotolerans, B. pulvifaciens, B. pumilus, B. purgationiresistens, B. pycnus, B. qingdaonensis, B. qingshengii, B. reuszeri, B. rhizosphaerae, B. rigui, B. ruris, B. safensis, B. salarius, B. salexigens, B. saliphilus, B. schlegelii, B. sediminis, B. selenatarsenatis, B. selenitireducens, B. seohaeanensis, B. shacheensis, B. shackletonii, B. siamensis, B. silvestris, B. simplex, B. siralis, B. smithii, B. soli, B. solimangrovi, B. solisalsi, B. songklensis, B. sonorensis, B. sphaericus, B. sporothermodurans, B. stearothermophilus, B. stratosphericus, B. subterraneus, B. subtilis, B. s. subsp. inaquosorum, B. s. subsp. spizizenii, B. s. subsp. subtilis, B. taeanensis, B. tequilensis, B. thermantarcticus, B. thermoaerophilus, B. thermoamylovorans, B. thermocatenulatus, B. thermocloacae, B. thermocopriae, B. thermodenitrificans, B. thermoglucosidasius, B. thermolactis, B. thermoleovorans, B. thermophilus, B. thermoruber, B. thermosphaericus, B. thiaminolyticus, B. thioparans, B. thuringiensis, B. tianshenii, B. trypoxylicola, B. tusciae, B. validus, B. vallismortis, B. vedderi, B. velezensis,

*B. vietnamensis, B. vireti, B. vulcani, B. wakoensis, B. weihenstephanensis, B. xiamenensis, B. xiaoxiensis,* and *B. zhanjiangensis*. With a member of *Bacillus* as the microbe, the process can use a carrier from one of: liquid, water, dry humic acid, wet humic acid, urea, soil wetting aid or a penetrant.

In one embodiment, the penetrant can be about 20% alcohol ethoxylate and about 80% orange oil. Alternatively, surfactants can be added. The penetrant can have one or more high terpene (50% by weight or more) based oils, one or more stabilizers, one or more chelating agents, one or more preservatives, one or more acidic pH adjusters and one or more organic solvents.

The microbes can be: *Bacillus amyloliquefaciens* at 5.85×107^7 cfu/ml, *Bacillus* lichniformis at 1.80×107^7 cfu/ml, *Bacillus pumilus* at 4.05×107^7 cfu/ml, or *Bacillus subtilis* at 6.30×107^7 cfu/ml. Leonardite and urea and water can be used with the microbes. Polyloxy-(1,2-Ethanedily), Alpha-(nonylphenyl)-omega-hydroxy can be used with the microbes. The solution can also include Leonardite and water. The microbial solutions can be applied through spraying, wetting, dipping, misting, drenching, showering, fogging, soaking, dampening, drizzling, dousing and splashing.

Advantages of the solutions may include one or more of the following. Soil enrichment solutions of the system stimulate plant growth, rejuvenate the soil, and promote the growth of beneficial soil microorganisms. Some embodiments also provide natural pathogens for the prevention, control and/or cure of turf and plant diseases and other purposes encouraging germination and/or growth. The solutions contain microorganism spores and/or colonies that remain viable for at least about a year when stored at room temperature. The solutions provide soil enrichment solutions containing viable microorganism spores and/or colonies, particularly those useful for enriching poor, disturbed soils or soils having little or no microbial activity because of the heavy past use of chemicals and/or fertilizers. The systems provide solutions containing viable micro organism spores and/or colonies of beneficial fungicides that can be used for seed, turf, and leaf treatment for the prevention, control, and/or cure of turf and plant diseases and other beneficial purposes. The solutions also provide soil enrichment solutions containing microorganism spores and/or colonies that remain at least about 90% viable for up to at least about 12, preferably 18 months at room temperature, i.e., about 20° to 25° C.

These and other advantages are achieved by the present invention, which provides a method of preserving and solutions containing microbial spores and/or colonies.

BRIEF DESCRIPTION OF THE FIGURES

FIG. 1 shows an exemplary process to selectively breed the microbes for agricultural use.

FIG. 2 shows an exemplary process to produce the microbial products.

FIGS. 3A-3B show exemplary antifungal activity express by different *Bacillus* spp. strains.

FIG. 4 shows exemplary cellulolytic enzymes synthesized by the biological control agent which can be involved in two plant defense mechanism against phyto-pathogenic fungi.

FIG. 5 shows exemplary soil enhancement enzyme profiles isolation standards.

DETAILED DESCRIPTION OF THE INVENTION

A selectively bred microbial solution is disclosed with multiple single microbial series separately cultivated and followed with cross cultivation among those microbial series in a specific sequence and contains each of those microbial series, and by-products produced by those crossly cultivated microbial series are used for applications in modifying soil quality, activating soil, effectively degrading soil pollution, and helping growth of crops in a soil enhancement embodiment. After the selective breeding through the fermentation, the selectively bred naturally-occurring microorganisms have the ability to penetrate through the soil while enriching with micronutrients, microbial cultures and organic materials in a highly concentrated stage.

FIG. 1 shows an exemplary process to selectively breed the microbes for agricultural use. First, fermentation media are prepared with a nutrient supply (1). The nutrients can include a carbon source Dextrose or Glucose. Additional carbon sources can be used with the dextrose or glucose singly or in combination. For example, another carbon source can be sucrose, for example. Next, a nitrogen source is provide such as soy protein that has not been genetically modified (2). Next, in (3), micronutrients—Calcium, Magnesium and Zinc are provided. A person of ordinary skilled in the art appreciates that various compositions of the fermentation media can be prepared so long as the nutrients, one or more of the carbon sources, and the micronutrients are included.

In (4), the fermentation media is prepared using water supply and sterilized using stream sterilizer at 120 degrees Celsius for 45 minutes, but the temperature and time can be varied in accordance with tank volume. In (5), the process produces the microbial products, as is detailed in FIG. 2. At each stage, quality control methods are applied using standard plate count method for *Shigella, E. Coli, Salmonella Yersinia* and *Psuedomonas beroginosa* for their absence. All products are manufactured according to USEPA (United States Environmental Protection Agency) standards.

The microbes can be: *Bacillus amyloliquefaciens* at 5.85×107^7 cfu/ml, *Bacillus lichniformis* at 1.80×107^7 cfu/ml, *Bacillus pumilus* at 4.05×107^7 cfu/ml, or *Bacillus subtilis* at 6.30×107^7 cfu/ml. Leonardite and urea and water can be used with the microbes.

Polyloxy-(1,2-Ethanedily), Alpha-(nonylphenyl)-omega-hydroxy can be used with the microbes. The solution can also include Leonardite and water.

The Microbial Strain selection and profile of microbial genes are carefully selected to form the formulation of products. Through strain selections, screening and improvement, the system generates various bio-fertilizer products for rejuvenating soil and promote plant growth. For example, *Bacillus Subtilus* has 4,100 genes. These genes each contain approximately 2000 traits. Each one of these traits and its mutation has over 1000 profile and sub-profile.

With a member of *Bacillus* as the microbe, the process can include a carrier from one of: liquid, water, dry humic acid, wet humic acid, urea, soil wetting aid, or a penetrant. When applied in the field to plants, billions of the selectively bred bacteria operate to covert and breakdown organic matter into a form of micronutrient for plant uptake. The microbial solution can be applied through spraying, wetting, dipping, misting, drenching, showering, fogging, soaking, dampening, drizzling, dousing and splashing.

The biodiversity of *Bacillus* group and beneficial traits of *bacillus* species are useful in plant protection. *Bacillus* genus is widely spread in nature. *Bacillus* species such as *B. Subtilus, B. Megaterium, B. Amyloliquefaciens, B. lichniformis* are carefully selected, for their specific profile which contains beneficial traits for plant protection and growth promotion that comprise the synthesis in broad-spectrum with active metabolites and easily adaptation in various environment conditions that benefits plant bacterial interaction and advantageous of formulation process.

As plants roots exudates and lysates attracts and stimulate microbial activity in the root surrounding soil, the zhizosphere (chemical space around the roots) became highly populated. Beneficial *Bacillus* spp. strains can compete with other bacteria and fungi that could adversely affect crops. They can inhibit phytopathogenic attacks such as "Basal Stem Rot, *phytophthora, fusarium*", or induce host-plant defense system against potential pathogenic attacks, stimulate plant growth, improve nutrient uptake, and reduce negative environment traits.

Beneficial traits with agricultural purpose in *Bacillus Subtilis* and related species are detailed next. The species of bacillus group, particularly *B. Subtilus, B. Megaterium, B. Amyloliquefaciens, B. lichniformis* are extremely importance in agriculture, as phytopathogenic antagonist or plant growth promoters. It is often referring as "Plant Growth Promoting rhizobacteria" or PGPR. PGPR are naturally occurring soil bacteria that have the ability to colonize the roots, and the high concentration and the amount of bacteria artificially created (added) as detailed above enhances the stimulation of plant growth by phytohormones production or by releasing beneficial organic compounds.

Beside plant growth stimulation, *Bacillus Subtilis* and its related species strain are involved in plant protection against phyto-pathogenic attacks. They act directly against pathogens by producing extracellular lytic enzyme and secondary metabolites with inhibitory growth action or interfere by quorum quenching to disturb cell-to-cell communication of the infectious expression in pathogenic bacteria. They could also compete with plant pathogen for the available nutrient and niche. Another important role is the reduction of the infection process by inducing defense response in the host plant.

Each single microbial series is separately cultivated in its designated cultivation medium, and the optimal pH in the growing and reproduction of different microbial series also varies. Therefore, proper control and regulation of pH of the cultivation medium are provided in the course of bacterial cultivation and fermentation. The microbial series acquires energy through aerobic respiration. However, the aerobic respiration generally has to rely upon only the oxygen dissolved in the cultivation medium, i.e., the dissolved oxygen, and the containment of the dissolved oxygen in the cultivation medium is not always provided in sufficient amount and will be soonest consumed by bacteria since oxygen is difficult to get dissolved in water. Therefore, constant air supply to the microbial series is provided without interruption in the course of the cultivation and fermentation of the microbial series. Compositions of cultivation medium selected and the optimal growing environment conditions for each microbial series are detailed as follows:

When the cultivation of each microbial series is saturated in its cultivation medium, a cross cultivation is followed. The compound microbial preparation differs from a single bacteria species or a single microbial product for soil modification. In some embodiments, the microbial life activities from multiple preselected microbial series are provided that are mutually coordinated and contained for crops or plants to get the results of specific fertilizers; that is, multiple microorganisms are screened from the soil and selectively bred to become capable of improving nutrition of the crops, and then to provide nitrogen, phosphor, and potassium fertilizers important to the growth of the plants in organic means by taking advantage of interaction among compound microbial preparations. Wherein, the nitrogen fixing series fixes nitrogen molecules in the nature to make it a nitrogen source for manufacturing fertilizers; the phosphoric acid releasing series unlocks and converts insolvable phosphates in the soil into phosphor, ferrous, and calcium fertilizers; the yeast group series makes it available in the making of vitamins and growing hormones, and decomposes organics to improve disease-resistant sufficiency of the plants; the photosynthetic bacteria series while being applied in manufacturing of glucose secrets carotenoid and eliminates toxic substances including hydrogen sulfide and ammonia; the *actinomyces* series secrets antibiotic substances at a constant amount on long-term bases to inhibit diseases; and the growing factors producing series also releases on long-term basic a given amount of growing hormones to promote roots, stalks and leaves of crops or plants to grow strong. In some embodiments, one or more of the above described series of microbials are used.

In the course of cross cultivation, each of those eight microbial series maintains intrigue symbiosis and shared prosperity among one another by playing a critical role with secretions of its own particular active organics. For example, the nitrogen fixing series converts the molecular nitrogen into ammoniac nitrogen and the resultant ammoniac nitrogen is partially to be consumed by the nitrogen fixing series, the remaining ammoniac nitrogen is synthesized into organic nitrogen to be consumed by other bacterial series; and the yeast group series may catalyze polysaccharide into simple sugar including glucose to be consumed by *lactobacillus* to convert into alcohol. Centering on the photosynthetic bacteria series and the yeast group series as leading cores, each microbial series supports activities of other microbial series with its synthetic proficiency while taking advantage of those substances produced by other microbial series to constitute a commonwealth circle. However, behind the big chain of food that relies upon symbiosis substances, a survival game of gigantic resistance and wipe out takes place among one another due to different properties. In the environment seeing violent stimulation, new endocrines are produced. What's more important is that any strain of bacteria survived is practically the top selected one with reliable activities.

Depending on the locality, season, depth of soil, the present invention produces the proper strains of the microbial series. Those who are familiar with the art may apply on various series, e.g. coccus, *bacillus, vibrio*, or Spirillum; different demands of oxygen, e.g., aerobic and/or anaerobic; different environmental requirements, e.g., *acidophilus, alkalophilus*, psycho-, meso-, or thermophilic to come up with a locality-specific compound microbial preparation and different microbial series may be used to produce compound microbial preparations in various applications, e.g., for fertilizer, pesticide, or promotion growth of flowers and fruits.

Spores and/or colonies that enrich soils and/or provide plant biological control agents are employed in some embodiments. These include bacteria such as *Bacillus* species, e.g., *Bacillus subtilis, Bacillus cereus, Bacillus penetrans, Bacillus licheniformis*, and *Bacillus megaterium*; fungi such as *Trichoderma*, e.g., *Trichoderma hamatum, Trichoderma harzianum, Trichoderma polysporum, Trichoderma konigii, Trichoderma viride*; yeast such as *Saccharomyces cerevisiae*; and mixtures of these. Other examples are given hereafter.

Figures 3A, 3B:
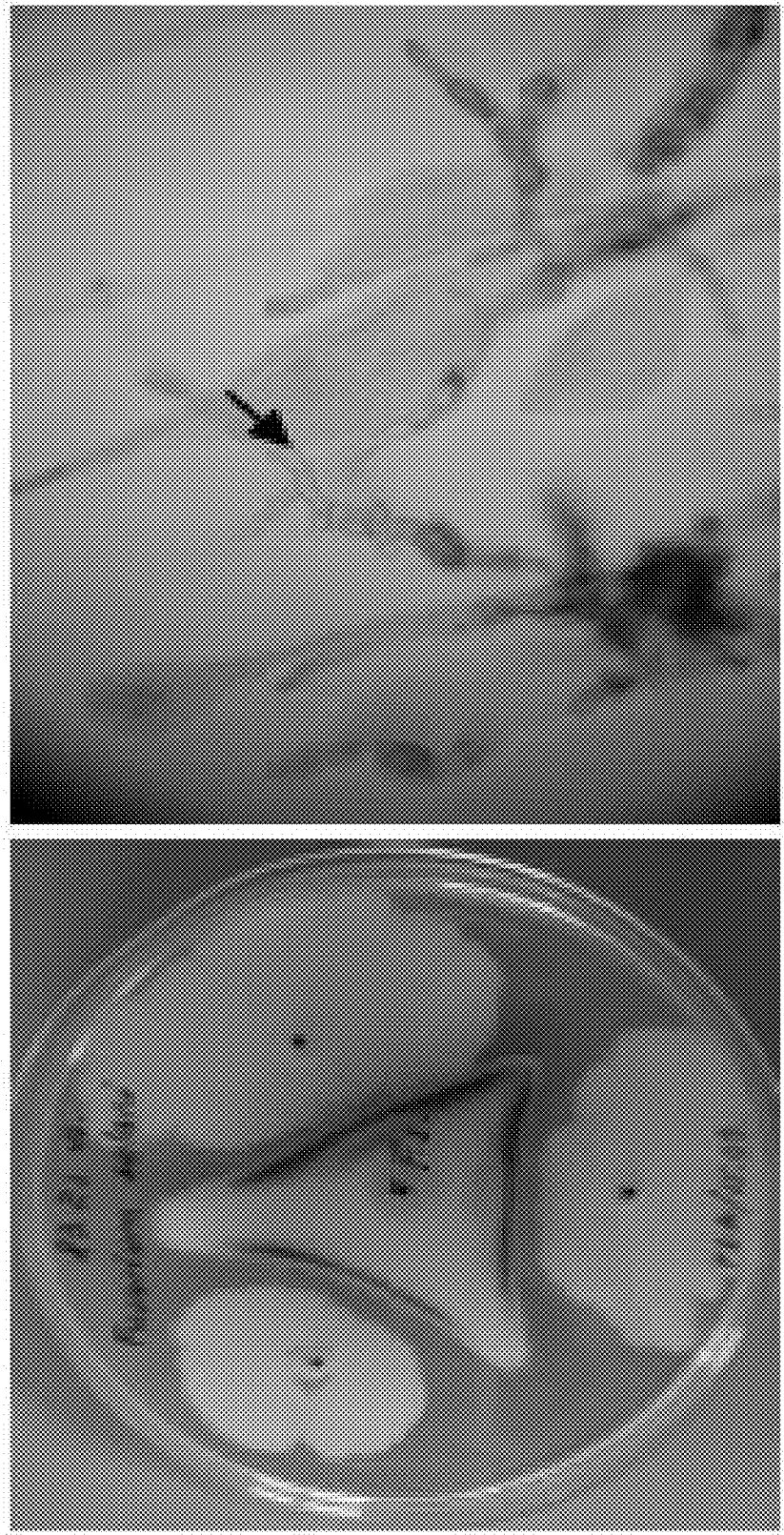

FIG. 3 shows exemplary antifungal activity express by different *Bacillus* spp. Strains. FIG. 3A shows exemplary

*Bacillus* spp. antagonistic activity against *fusarium solani*; while FIG. 3B shows exemplary fungal cell wall degradation, cell lysis and cytoplasm bleeding due to *Bacillus* spp. extracellular enzymes.

Figure 4:
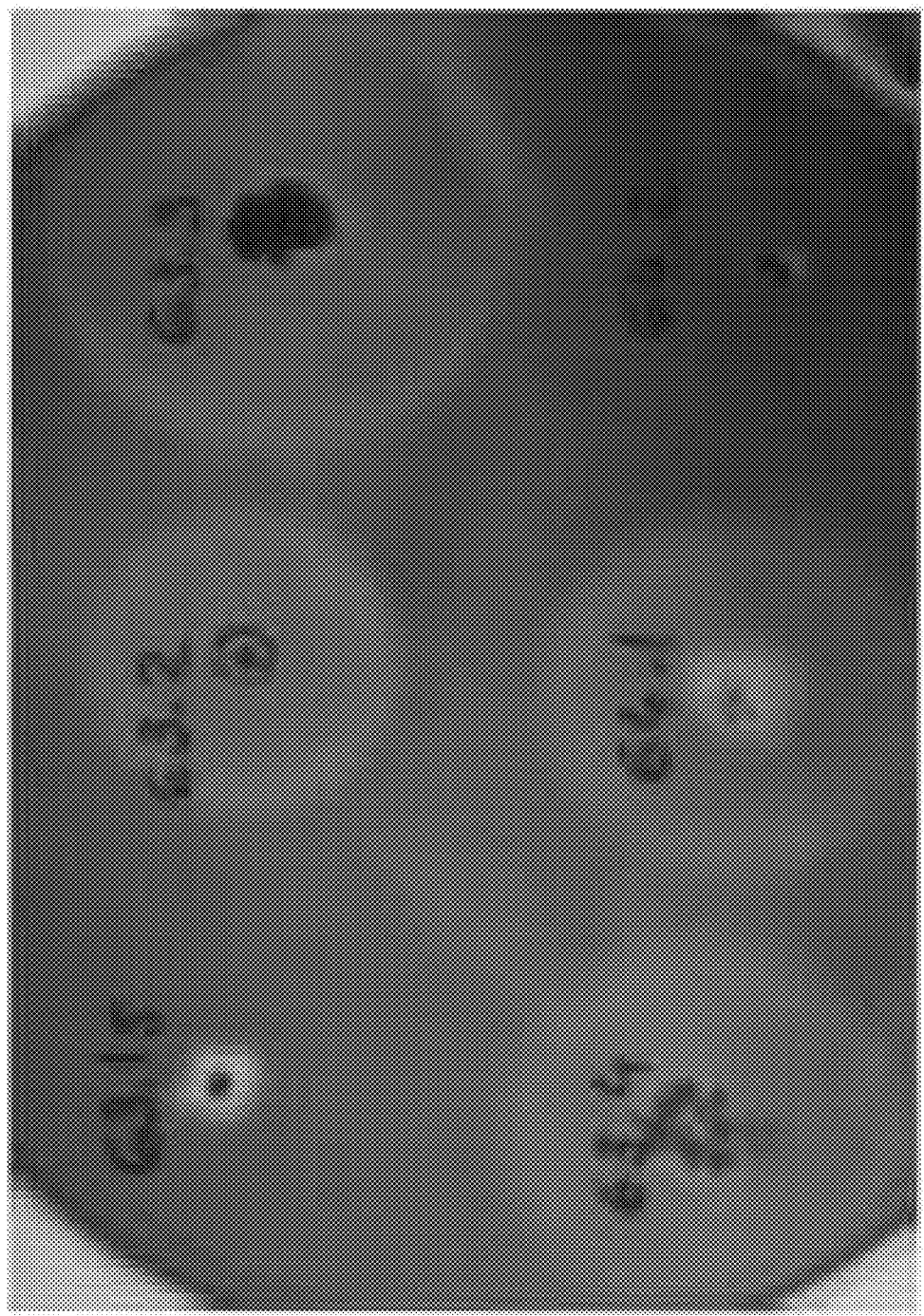
Figure 5:
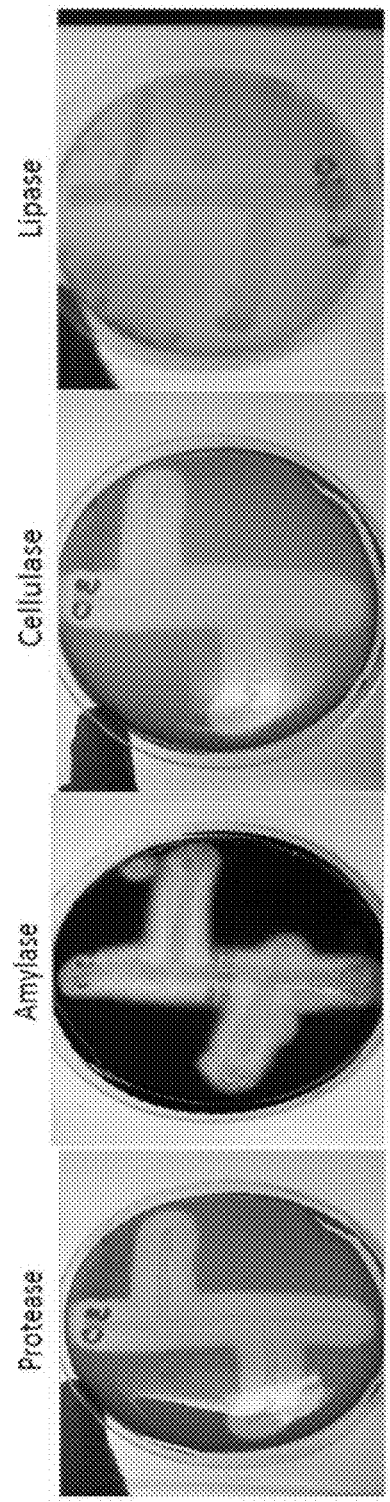

FIG. 4 shows exemplary cellulolytic enzymes synthesized by the biological control agent which can be involved in two plant defense mechanism against phyto-pathogenic fungi. Exemplary cellulase activity exposed on Luria Bertani medium supplement with carboxyl-methyl cellulose, reveal a clear halo of CMC degradation, after two days of *Bacillus* spp. strains incubation.

In one embodiment called AGN, a natural microbial soil rejuvenation and enrichment provides microbials including enzymes, metabolites and beneficial microbial biomass that aid in building soil structure. In this embodiment, the concentration of microbes can include the following:

*Bacillus amyloliquefaciens* $5.85 \times 10^7$ cfu/ml
*Bacillus* lichniformis $1.80 \times 10^7$ cfu/ml
*Bacillus pumilus* $4.05 \times 10^7$ cfu/ml
*Bacillus subtilis* $6.30 \times 10^7$ cfu/ml and the penetrant can be water with Polyloxy-(1,2-Ethanedily), alpha-(nonylphenyl)-omega-hydroxy or Alcohol Ethoxylate.

The colony-forming unit (CFU or cfu) is a measure of viable bacterial or fungal cells. CFU measures only viable cells. For convenience the results are given as CFU/mL (colony-forming units per milliliter) for liquids, and CFU/g (colony-forming units per gram) for solids.

Humic Acid can be leonardite and water, and the penetrant can be water with Polyloxy-(1,2-Ethanedily), alpha-(nonylphenyl)-omega-hydroxy. Humic Acid provides the necessary amino acids and protein to support an active microbial population to support active and healthy plant growth.

Penetrants or non-ionic penetrants facilitate even water movement into the soil both horizontally and vertically while maintaining a very low volatility. In some embodiments, the penetrants comprises a surfactant, which can be used together with heptonic acid, alkyl polyglycoside, water soluble polyacrylamides (PAMs), and/or polysiloxane emulsion. In some embodiments, the penetrants are selected to maintain soil moisture level near to root zone of predetermined plants, prevent leaching of nutrients, or both. Other surfactants can be used in various embodiments, for example: Nonionic surfactants include agents such as sorbitan monolaurate, sorbitan monopalmitate, sorbitan sesquioleate, sorbitan trioleate, polyoxyethylene sorbitan monolaurate, polyoxyethylene sorbitan monostearate, polyethylene glycol monooleate, polyethylene glycol alkylate, polyoxyethylene alkyl ether, polyglycol diether, lauroyl diethanolamide, fatty acid iso-propanolamide, maltitol hydroxy fatty acid ether, alkylated polysaccharide, alkyl glucoside, sugar ester, oleophillic glycerol monostearate, self-emulsifiable glycerol monostearate, polyglycerol monostearate, polyglycerol alkylate, sorbitan monooleate, polyethylene glycol monostearate, polyoxyethylene sorbitan monooleate, polyoxyethylene cetyl ether, polyoxyethylene sterol, polyoxyethylene lanolin, polyoxyethylene bees wax, and polyoxyethylene hydrogenated castor oil; and the like. Anionic surfactants include agents such as sodium stearate, potassium palmitate, sodium cetyl sulfate, sodium lauryl phosphate, sodium polyoxyethylene lauryl sulfate, triethanolamine palmitate, polyoxyethylene sodium lauryl phosphate, and sodium N-acyl glutamate; and the like. Cationic surfactants include agents such as stearyl dimethylbenzyl ammonium chloride, stearyl trimethyl ammonium chloride, benzalkonium chloride, and laurylamine oxide; and the like.

In one embodiment, the penetrant can be about 20% alcohol ethoxylate and about 80% orange oil. The penetrant can have one or more high terpene (50% by weight or more) based oils, one or more stabilizers, one or more chelating agents, one or more preservatives, one or more acidic pH adjusters and one or more organic solvents.

Surfactants can be used. Nonionic surfactants include agents such as sorbitan monolaurate, sorbitan monopalmitate, sorbitan sesquioleate, sorbitan trioleate, polyoxyethylene sorbitan monolaurate, polyoxyethylene sorbitan monostearate, polyethylene glycol monooleate, polyethylene glycol alkylate, polyoxyethylene alkyl ether, polyglycol diether, lauroyl diethanolamide, fatty acid iso-propanolamide, maltitol hydroxy fatty acid ether, alkylated polysaccharide, alkyl glucoside, sugar ester, oleophillic glycerol monostearate, self-emulsifiable glycerol monostearate, polyglycerol monostearate, polyglycerol alkylate, sorbitan monooleate, polyethylene glycol monostearate, polyoxyethylene sorbitan monooleate, polyoxyethylene cetyl ether, polyoxyethylene sterol, polyoxyethylene lanolin, polyoxyethylene bees wax, and polyoxyethylene hydrogenated castor oil; and the like. Anionic surfactants include agents such as sodium stearate, potassium palmitate, sodium cetyl sulfate, sodium lauryl phosphate, sodium polyoxyethylene lauryl sulfate, triethanolamine palmitate, polyoxyethylene sodium lauryl phosphate, and sodium N-acyl glutamate; and the like. Cationic surfactants include agents such as stearyl dimethylbenzyl ammonium chloride, stearyl trimethyl ammonium chloride, benzalkonium chloride, and laurylamine oxide; and the like. Amphoteric surfactants such as alkylaminoethyl glycine chloride and lecithin; and the like.

To deploy, field persons mix AGN with clean water and let it set for a minimum of 1 hour or maximum overnight (keep air flows after mixed with water) and apply directly to moist soil as a pre-plant, post-plant or seasonal treatment. The solution can be applied to soil, seeds, and plants. In some embodiments, the solution is not mixed with any other fertilizers or fungicides and deployment of such chemicals should wait at least 72 hours before or after treatment.

For tank mixing, in one embodiment, field personnel can mix 1 gallon (4 quarts or 3.8 liters) of AGN with minimum 100 gallons up to 1000 gallons of clean water in a clean tank and free of chemical. The solution can be applied at a rate of 2 to 4 quarts per surface acre or 4 to 8 liters per surface hectare.

For injection irrigation or fertigation, after tank mixing, AGN can be applied by dosage rate of 0.5 to 1 gallon (2 to 4 quarts) per surface acre (4 to 8 liters per surface hectare). For side-dress or starter, the solution can be applied at a rate of 1 to 2 quarts per surface acre or 2 to 4 liters per surface hectare. Preferably, the solution can be dispensed with:

Localized Drip or Trickle
Sprinkler, or
Contour Furrows

AGN includes Advanced Microbes for Soil Rejuvenation and creates a balanced soil environment for healthy plant growth which requires the ability to fully access the soil particulates and enriching them with phytonutrients utilizing highly concentrated microorganisms and organic materials.

The application of AGN creates superior root systems which can efficiently assimilate nutrients and micronutrients in the soil, resulting in higher yields and better plant health for all types of plants, crops, and trees and increases yields, soil-root-plant health, balance soil nutrients, penetrate and loosen clay soils, leach salts from root zones, reduce harmful nematodes, increase nutrient and micronutrient uptake as well as increase cathode ion transfer.

Any microbial spores and/or colonies can be preserved using methods and solutions of some embodiments. Spores and/or colonies of beneficial soil and plant pathogen biological control microorganisms are preferred. Microorganisms that grow rapidly and colonize substrata in soil after treatment with compositions of the invention are particularly preferred. These include, but are not limited to bacteria, e.g., *Bacillus* species such as *Bacillus subtilis, Bacillus cereus, Bacillus penetrans, Bacillus licheniformis*, and *Bacillus megaterium*; fungi, e.g., *Trichoderma* species such as *Trichoderma hamatum, Trichoderma harzianum, Trichoderma polysporum, Trichoderma konigii*, and *Trichoderma viride*; and yeast species such as *Saccharomyces cerevisiae*. As illustrated below, mixtures of microorganisms can also be preserved, and are preferred in many embodiments. Examples are given hereafter.

In the practice of the system, spores or whole microorganisms, including harvested and/or lyophilized microbial colonies containing spores, are added to solutions. The solutions can be formulated for any use requiring viable microbial spores and/or colonies such as for fertilizers, composting, food products, and pharmaceutical compositions. Liquid fertilizers are preferred for soil enrichment purposes. Water miscible dry powders and/or granules such as lyophilized preparations of spores and/or colonies are preferred in many embodiments. The amount of spores or microorganisms added to solutions of the invention is not fixed per se, and necessarily is dependent upon the degree of soil and/or plant remediation required, the number and identity of microorganism species needed in the formulation, and the concentration of other ingredients in the formulation. Preferred embodiments employ spores and/or colonies in amounts effective to achieve recolonization of the soil by spray application of the composition. Typical embodiments contain sufficient spores and/or colonies to deliver from about 1000 to about 1,000,000 colony forming units (CFU) per square foot when the preparation is delivered.

Preservative solutions of some embodiments are colloidal in nature, containing humic acid and/or other organic macromolecules. By "colloidal" is meant a state of matter which comprises either large molecules, aggregations of smaller molecules, or a combination of the two. Some embodiments contain large molecules such as humic acid and/or methylene urea compounds of varying chain length. The particles are surrounded by different matter such that a dispersed phase is surrounded by an external phase. Both phases may be solid or liquid (and sometimes gaseous). One phase comprises water in most embodiments; typical ranges are from about 35% to about 58% by weight water in the total composition, but some embodiments contain less than about 20% by weight water in the total composition.

Microorganisms and/or their spores which can be preserved using formulations of the invention further exhibit a number of desirable characteristics related to soil enrichment and improvement of soil quality described above, such as biological control of plant pathogens (already mentioned); enhancement and/or production of desirable phtyohormones, e.g., auxins, giberillins and cytokinins; and solubilization of phosphates. Certain strains of *Bacillus subtilis*, for example, inhibit *N. Galligena* that colonize apple branch scars if applied to trees after leaf fall. *E. herbicola* and *Pseudomonas* isolates have been shown to partially control fire blight of pome fruit trees. Several *Bacillus* species produce antibiotics useful when sprayed as a leaf or needle application on tobacco, Douglas fir, and apple trees, and the natural protection of leaves provided by the buffering capacity of phylloplane microorganisms has been demonstrated. *Azobacter, Rhizobium, Bacillus, Klebsiella, Azospirillium, Enterobacter, Serratia, Agrobacterium, Arthrobacter, Aerobacter, Actinomyces, Bacillus, Pseudomonas*, and other bacteria stimulate growth, increase yield, and produce other positive results by various mechanisms including enhancing nutrient uptake, increasing germination, enhancing seedling emergence, stimulating de novo biosynthesis, and the like, when applied to fields of various food plants.

The resulting solutions supply carbon-rich organic materials in a bioavailable form for soils and plants together with nutrients that feed the microorganisms as they multiply after application. Solutions of some embodiments provide an excellent food source for the germination of spores and/or colonies when the solutions are applied to soil or water. It is a further advantage that preferred solutions contain a wide variety of naturally occurring metabolites that can be readily absorbed by the growing microorganisms and enhance seed germination, root development, and growth of plants in the soil.

As summarized above, some embodiments are formulated with microorganism spores and/or cultures useful in the prevention, control and/or cure of plant diseases, particularly those of fungal origin. Illustrative examples are provided hereafter. One embodiment, for example, maintains the viability of *Bacillus subtilis* GB03 (EPA Reg. No. 7501-144), a bacteria recognized to colonize developing root systems, suppressing disease organisms such as *Fusarium, Rhizoctonia, Alternaria* and *Aspergillus* that attack root systems. Compositions of the invention can be used to treat developed root systems as well as developing root systems. As the root system develops, grows, and functions, the bacteria grow with the roots, extending protection throughout the growing season. As a result of this biological protection, a vigorous root system can be established and maintained by the plants.

In addition, *B. subtilis* GB03 has been shown to increase the amount of nodulation by nitrogen-fixing bacteria when used on many legumes. This improvement in nodulation is a result of a healthier root system, allowing more sites for nodules to form from naturally-occurring soilborne nitrogen-fixing bacteria. Illustrative examples follow.

FIG. 5 shows an exemplary AGN enzyme profiles isolation standard. Soil bacteria in the genus *Bacillus* are well known for contributions to improving soil structure, nutrient availability and as a competitive excluder to harmful pathogens. *Bacillus* lichniformis produces a variety of extracellular enzymes that are associated with the cycling of nutrients in nature, thus improve nutrient availability and nutrient uptake. *Bacillus pumilus* is an agricultural fungicide. Growth of the bacterium on plant roots prevents *rhizoctonia* and *fusarium* spores from germinating. These strains are heavily involved with inhibition of opportunistic pathogens as well as improving nutrient availability and nutrient uptake. *Bacillus subtilis* does nitrogen fixing; produce inhibitory compounds that reduce the growth of harmful microorganism. It interfere with the germination of plant pathogen spores and their attachment to host plants, acts as a prebiotic conditioning plants own defense mechanisms prior to attack from potential pathogens. *Bacillus amyloliquefaciens* had anti fungal properties and help nitrogen fixing availability. *Bacillius megaterium* is a plant growth-promoting rhizobacteria (PGPR) and phosphate solubilizing. It promotes the activation of plant defense responses and secretion of plant growth-regulating substances such as auxins, cytokinins and bacterial volatiles. Phytohormones are involved in the control of growth and in almost every important developmental process in plants. Bacterial secretion of phytohormones can impact root architecture by overproduction of root hairs and lateral roots and subsequently increased nutrient and water uptake, thus contributing to growth.

Example 1 (AGN)

Microbes:
  Bacillus amyloliquefaciens at 5.85×10^7 cfu/ml
  Bacillus lichniformis at 1.80×10^7 cfu/ml
  Bacillus pumilus at 4.05×10^7 cfu/ml
  Bacillus subtilis at 6.30×10^7 cfu/ml
Humic Acid: Leonardite and H2O
Nitrogen: Urea and H2O
Penetrant: Polyloxy-(1,2-Ethanedily), Alpha-(nonylphenyl)-omega-hydroxy and H2O Example 2 (AGN LTE)

Microbes:
  Bacillus amyloliquefaciens at 5.85×10^7 cfu/ml
  Bacillus lichniformis at 1.80×10^7 cfu/ml
  Bacillus pumilus at 4.05×10^7 cfu/ml
  Bacillus subtilis at 6.30×10^7 cfu/ml
Humic Acid: Leonardite and H2O The above description is for the purpose of illustrating and not limiting the present invention, and teaching the person of ordinary skill in the art how to practice the invention. It is not intended to detail all those obvious modifications and variations of it which will become apparent to the skilled worker upon reading the description. It is intended, however, that all such obvious modifications and variations be included within the scope of the present invention as defined in the appended claims. The claims are meant to cover the claimed components and steps in any sequence which is effective to meet the objectives there intended, unless the context specifically indicates the contrary.

The patents, papers, and book excerpts cited above are hereby incorporated herein by reference in in their entireties.

What is claimed is:

1. A method for enhancing soil, comprising:
   preparing a microbial solution with microbes, a growth medium, and water;
   iteratively and selectively breeding generations of microbes for microbial strain selection with predetermined microbial gene profiles to arrive at a predetermined microbial solution in a highly concentrated form of at least $1\times10^7$ cfu/ml (colony-forming units per milliliter), wherein multiple single microbial series are separately cultivated and followed with cross cultivation among the microbial series in a specific sequence, and by-products produced by the crossly cultivated microbial series are provided as a highly concentrated solution;
   adding humic acid with amino acids and protein to the concentrated solution to promote an active microbial population to support active and healthy plant growth; and
   storing the microbial solution in a container for application as a soil amendment that is applied to the soil.

2. The method of claim 1, comprising selecting a member of Bacillus as the microbe and providing a carrier from one of: liquid, water, dry humic acid, wet humic acid, urea, or a penetrant.

3. The method of claim 1, wherein the growth medium comprises a carbon source.

4. The method of claim 1, wherein the growth medium comprises sugar, molasses, or maltodextrin.

5. The method of claim 1, comprising mixing the solution with 1 part microbes, 10 part carbon source, and 1000 parts water.

6. The method of claim 1, comprising aerating the solution for at least 20 minutes before applying to the soil.

7. The method of claim 1, comprising selecting the microbe from Bacillus (B.) acidiceler, B. acidicola, B. acidiproducens, B. acidocaldarius, B. acidoterrestrisr, B. aeolius, B. aerius, B. aerophilus, B. agaradhaerens, B. agri, B. aidingensis, B. akibai, B. alcalophilus, B. algicola, B. alginolyticus, B. alkalidiazotrophicus, B. alkalinitrilicus, B. alkalisediminis, B. alkalitelluris, B. altitudinis, B. alveayuensis, B. alvei, B. amyloliquefaciens, B. a. subsp. amyloliquefaciens, B. a. subsp. plantarum, B. amylolyticus, B. andreesenii, B. aneurinilyticus, B. anthracis, B. aquimaris, B. arenosi, B. arseniciselenatis, B. arsenicus, B. aurantiacus, B. arvi, B. aryabhattai, B. asahii, B. atrophaeus, B. axarquiensis, B. azotofixans, B. azotoformans, B. badius, B. barbaricus, B. bataviensis, B. beijingensis, B. benzoevorans, B. beringensis, B. berkeleyi, B. beveridgei, B. bogoriensis, B. boroniphilus, B. borstelensis, B. brevis Migula, B. butanolivorans, B. canaveralius, B. carboniphilus, B. cecembensis, B. cellulosilyticus, B. centrosporus, B. cereus, B. chagannorensis, B. chitinolyticus, B. chondroitinus, B. choshinensis, B. chungangensis, B. cibi, B. circulans, B. clarkii, B. clausii, B. coagulans, B. coahuilensis, B. cohnii, B. composti, B. curdlanolyticus, B. cycloheptanicus, B. cytotoxicus, B. daliensis, B. decisifrondis, B. decolorationis, B. deserti, B. dipsosauri, B. drentensis, B. edaphicus, B. ehimensis, B. eiseniae, B. enclensis, B. endophyticus, B. endoradicis, B. farraginis, B. fastidiosus, B. fengqiuensis, B. firmus, B. flexus, B. foraminis, B. fordii, B. formosus, B. fortis, B. fumarioli, B. funiculus, B. fusiformis, B. galactophilus, B. galactosidilyticus, B. galliciensis, B. gelatini, B. gibsonii, B. ginsengi, B. ginsengihumi, B. ginsengisoli, B. globisporus, B. g. subsp. globisporus, B. g. subsp. marinus, B. glucanolyticus, B. gordonae, B. gottheilii, B. graminis, B. halmapalus, B. haloalkaliphilus, B. halochares, B. halodenitrificans, B. halodurans, B. halophilus, B. halosaccharovorans, B. hemicellulosilyticus, B. hemicentroti, B. herbersteinensis, B. horikoshii, B. horneckiae, B. horti, B. huizhouensis, B. humi, B. hwajinpoensis, B. idriensis, B. indicus, B. infantis, B. infernus, B. insolitus, B. invictae, B. iranensis, B. isabeliae, B. isronensis, B. jeotgali, B. kaustophilus, B. kobensis, B. kochii, B. kokeshiiformis, B. korensis, B. korlensis, B. kribbensis, B. krulwichiae, B. laevolacticus, B. larvae, B. laterosporus, B. lautus, B. lehensis, B. lentimorbus, B. lentus, B. licheniformis, B. ligniniphilus, B. litoralis, B. locisalis, B. luciferensis, B. luteolus, B. luteus, B. macauensis, B. macerans, B. macquariensis, B. macyae, B. malacitensis, B. mannanilyticus, B. marisflavi, B. marismortui, B. marmarensis, B. massiliensis, B. megaterium, B. mesonae, B. methanolicus, B. methylotrophicus, B. migulanus, B. mojavensis, B. mucilaginosus, B. muralis, B. murimartini, B. mycoides, B. naganoensis, B. nanhaiensis, B. nanhaiisediminis, B. nealsonii, B. neidei, B. neizhouensis, B. niabensis, B. niacini, B. novalis, B. oceanisediminis, B. odysseyi, B. okhensis, B. okuhidensis, B. oleronius, B. oryzaecorticis, B. oshimensis, B. pabuli, B. pakistanensis, B. pallidus, B. pallidus, B. panacisoli, B. panaciterrae, B. pantothenticus, B. parabrevis, B. paraflexus, B. pasteurii, B. patagoniensis, B. peoriae, B. persepolensis, B. persicus, B. pervagus, B. plakortidis, B. pocheonensis, B. polygoni, B.

*polymyxa, B. popilliae, B. pseudalcalophilus, B. pseudofirmus, B. pseudomycoides, B. psychrodurans, B. psychrophilus, B. psychrosaccharolyticus, B. psychrotolerans, B. pulvifaciens, B. pumilus, B. purgationiresistens, B. pycnus, B. qingdaonensis, B. qingshengii, B. reuszeri, B. rhizosphaerae, B. rigui, B. ruris, B. safensis, B. salarius, B. salexigens, B. saliphilus, B. schlegelii, B. sediminis, B. selenatarsenatis, B. selenitireducens, B. seohaeanensis, B. shacheensis, B. shackletonii, B. siamensis, B. silvestris, B. simplex, B. siralis, B. smithii, B. soli, B. solimangrovi, B. solisalsi, B. songklensis, B. sonorensis, B. sphaericus, B. sporothermodurans, B. stearothermophilus, B. stratosphericus, B. subterraneus, B. subtilis, B. s.* subsp. *inaquosorum, B. s.* subsp. *spizizenii, B. s.* subsp. *subtilis, B. taeanensis, B. tequilensis, B. thermantarcticus, B. thermoaerophilus, B. thermoamylovorans, B. thermocatenulatus, B. thermocloacae, B. thermocopriae, B. thermodenitrificans, B. thermoglucosidasius, B. thermolactis, B. thermoleovorans, B. thermophilus, B. thermoruber, B. thermosphaericus, B. thiaminolyticus, B. thioparans, B. thuringiensis, B. tianshenii, B. trypoxylicola, B. tusciae, B. validus, B. vallismortis, B. vedderi, B. velezensis, B. vietnamensis, B. vireti, B. vulcani, B. wakoensis, B. weihenstephanensis, B. xiamenensis, B. xiaoxiensis,* and *B. zhanjiangensis.*

8. The method of claim 1, comprising:
   applying enzymes, metabolites and microbial biomass to aid in building soil structure; and
   applying penetrants to facilitate even water movement into the soil both horizontally and vertically while maintaining low volatility.

9. The method of claim 1, comprising mixing the microbial solution with water and setting the solution for at least one hour and flowing air after mixing with water; applying the set solution directly to moist soil as a pre-plant, post-plant or seasonal treatment; and applying fertilizers or fungicides after delaying at least 72 hours before or after soil treatment.

10. The method of claim 1, wherein the microbes comprise Microbes *Bacillus amyloliquefaciens* at $5.85 \times 10^7$ cfu/ml, *Bacillus lichniformis* at $1.80 \times 10^7$ cfu/ml, *Bacillus pumilus* at $4.05 \times 10^7$ cfu/ml, or *Bacillus subtilis* at $6.30 \times 10^7$ cfu/ml.

* * * * *